United States Patent
Oakley et al.

(10) Patent No.: US 9,987,429 B2
(45) Date of Patent: Jun. 5, 2018

(54) DISPLAY ASSEMBLY AND DISPENSING DEVICE

(71) Applicant: Sanofi, Paris (FR)

(72) Inventors: Tom Oakley, Cambridge (GB); Stuart Milne, Buckden St. Neots (GB)

(73) Assignee: Sanofi, Paris (FR)

(*) Notice: Subject to any disclaimer, the term of this patent is extended or adjusted under 35 U.S.C. 154(b) by 97 days.

(21) Appl. No.: 14/904,720

(22) PCT Filed: Jul. 17, 2014

(86) PCT No.: PCT/EP2014/065328
§ 371 (c)(1),
(2) Date: Jan. 13, 2016

(87) PCT Pub. No.: WO2015/007809
PCT Pub. Date: Jan. 22, 2015

(65) Prior Publication Data
US 2016/0158448 A1    Jun. 9, 2016

(30) Foreign Application Priority Data
Jul. 17, 2013    (EP) .................................... 13176851

(51) Int. Cl.
*A61M 5/31* (2006.01)
*A61M 5/315* (2006.01)
*A61M 5/24* (2006.01)

(52) U.S. Cl.
CPC .......... *A61M 5/31* (2013.01); *A61M 5/31553* (2013.01); *A61M 2005/2411* (2013.01);
(Continued)

(58) Field of Classification Search
CPC ...... A61M 5/31553; A61M 2005/2411; A61M 2005/3126; A61M 2205/583
(Continued)

(56) References Cited

U.S. PATENT DOCUMENTS 5,961,495 A    10/1999    Walters et al.
6,004,297 A    12/1999    Steenfeldt-Jensen et al.
(Continued)

FOREIGN PATENT DOCUMENTS

DE    3645245    1/1994
DE    29703820    7/1998
(Continued)

OTHER PUBLICATIONS

Rote Liste, "50. Hypophysen-, Hypothalamushormone, andere regulatorische Peptide u. ihre Hemmstoffe," Chapter 50, ed. 2008, 20 pages.
(Continued)

*Primary Examiner* — Manuel Mendez
(74) *Attorney, Agent, or Firm* — Fish & Richardson P.C.

(57) ABSTRACT

A display assembly is proposed, comprising: a body (4) defining a window (17) having an axial extension, an indication member (2) for providing information to be displayed in the window (17), wherein the indication member (2) is movable relative to the body (4) for changing the information displayed in the window (17), a selection member (3), wherein the selection member (3) defines a masking section (45) and a non-masking section (46), the selection member (3) is rotatable around a rotation axis (x) with respect to the body (4) and with respect to the indication member (2), the non-masking section (46) and the masking section (45) partially overlap with the window (17) to define a displayed section (52) of the indication member (2), and wherein the selection member (3) and the indication member (2) are coupled such that the displayed section (52) of the indication member (2) is axially displaced within the window (17).

18 Claims, 4 Drawing Sheets

(52) U.S. Cl.
CPC ............... *A61M 2005/3126* (2013.01); *A61M 2205/583* (2013.01)

(58) Field of Classification Search
USPC .......................... 604/189, 63, 135, 136, 157
See application file for complete search history.

(56) References Cited

U.S. PATENT DOCUMENTS

| | | | |
|---|---|---|---|
| 6,048,336 | A | 4/2000 | Gabriel |
| 6,228,067 | B1 | 5/2001 | Gabriel |
| 6,899,699 | B2 | 5/2005 | Enggaard |
| 7,427,275 | B2 | 9/2008 | Deruntz et al. |
| 2006/0258988 | A1 | 11/2006 | Keitel et al. |
| 2008/0269688 | A1 | 10/2008 | Colucci et al. |
| 2008/0306445 | A1 | 12/2008 | Burren et al. |
| 2008/0306446 | A1 | 12/2008 | Markussen |
| 2009/0048561 | A1 | 2/2009 | Burren et al. |
| 2010/0168677 | A1 | 7/2010 | Gabriel et al. |
| 2010/0274198 | A1 | 10/2010 | Bechtold |

FOREIGN PATENT DOCUMENTS

| | | |
|---|---|---|
| DE | 10232412 | 2/2004 |
| DE | 69629391 T2 | 6/2004 |
| DE | 20317377 | 3/2005 |
| DE | 102005008280 | 7/2006 |
| DE | 102005063311 | 8/2006 |
| DE | 102005044096 | 11/2006 |
| DE | 102005023824 | 12/2006 |
| DE | 102005060929 | 3/2007 |
| DE | 202008011175 | 1/2010 |
| EP | 0762904 | 3/1997 |
| EP | 1181938 | 2/2002 |
| EP | 1304129 | 4/2003 |
| EP | 1819382 | 8/2007 |
| EP | 2806925 | 12/2014 |
| WO | WO 00/41754 | 7/2000 |
| WO | WO 2006/040296 | 4/2006 |
| WO | WO 2008/116766 | 10/2008 |
| WO | WO 2010/056367 | 5/2010 |
| WO | WO 2011/060785 | 5/2011 |
| WO | WO 2011/101349 | 8/2011 |
| WO | WO 2013/110538 | 8/2013 |

OTHER PUBLICATIONS

Extended European Search Report in Application No. 13176851.7, dated Feb. 21, 2014, 7 pages.
International Preliminary Report on Patentability in Application No. PCT/EP2014/065328, issued Jan. 19, 2016, 8 pages.
International Search Report and Written Opinion in International Application No. PCT/EP2014/065328, dated Sep. 25, 2014, 10 pages.

DISPLAY ASSEMBLY AND DISPENSING DEVICE

CROSS-REFERENCE TO RELATED APPLICATIONS

This application is a U.S. national stage application under 35 USC § 371 of International Application No. PCT/EP2014/065328, filed on Jul. 17, 2014, which claims priority to European Patent Application No. 13176851.7, filed on Jul. 17, 2013, the entire contents of which are incorporated herein by reference.

The present disclosure relates to a display assembly. Further, the present disclosure relates to a dispensing device. Expediently, the display assembly is used for the dispensing device. Furthermore, a dispensing device comprising the display assembly is disclosed.

Display assemblies are used to display information which can be retrieved from the display by a user, for example.

It is an object of the present disclosure to provide a novel or improved display assembly. Particularly, a display assembly which is suitable for a dispensing device should be provided.

This object is achieved, for example, by the independent claim. Further advantages, developments and refinements are subject-matter of dependent claims. However, in addition to the claimed subject-matter, the present disclosure may also contain advantageous embodiments which are currently not claimed, but readily disclosed to be claimed, if so desired.

An aspect of the present disclosure relates to a display assembly.

Another aspect relates to a dispensing device, e.g. a medical dispensing device. The dispensing device may be a fluid dispenser. Preferably, the display assembly is intended to be used for the dispensing device or the dispensing device comprises the display assembly.

Accordingly, as the display assembly is intended for use with a dispensing device and as the dispensing device may comprise the display assembly, features which are described above and below in conjunction with the display assembly may also relate to the dispensing device and vice versa.

The dispensing device may be designed to dispense a substance, e.g. a fluid, when actuated. The dispensing device may have a dispensing end. The substance dispensed from the device may leave the device via its dispensing end, when the device is operated to dispense the substance. The dispensing device may be a medical device, such as a dispenser of an antiseptic cream, an analgesic cream, a detergent or the like. Particularly, the dispensing device may be a drug delivery device wherein the substance dispensed comprises a drug, preferably a drug for treatment of a certain illness. The drug delivery device may be an injector, such as an autoinjector or a manually operated injector. The drug delivery device may be a pen-type device such as a pen injector. Furthermore, non-medical devices may be used for the dispensing device. The dispensing device may be a device for dispensing adhesives, lubricants, paints, detergents and so on.

The dispensing device may be a device which requires operation by a professional, such as a medically trained professional, or not. For example, the device may be a consumer device, e.g. a device which can also be operated by untrained persons and is specifically designed to be operated by untrained persons.

The dispensing device may be a food dispenser, particularly a dispenser for dispensing non-rigid foods, such as tomato sauce, cheese, butter, juice, smoothies, soup, coffee, tea, jam, peanut butter and so on. Also, rigid substances like crushed garlic, for example, may be dispensed using the dispensing device.

In an embodiment, the display assembly is used to display the size of a dose of substance which should be dispensed by the dispensing device. The display assembly may provide a dose display mechanism. The dispensing device may be a device in which the size of the dose to be dispensed by the device may be varied, particularly varied by the user of the device. When the dose is set, the information displayed by the display assembly may change continuously such that always the size of the currently set dose is displayed until the desired size has been reached. When the dose is dispensed, the displayed information may also change, for example indicating the remaining amount of substance to be dispensed to complete dispensing of the whole dose which was previously set.

In an embodiment, the display assembly comprises a body. The body may be a housing of the display assembly. Particularly, the body may be an outer housing of the dispensing device. The body of the display assembly may define a window. Through the window, information may be displayed by the display assembly. The window may have an axial extension, preferably a distinct axial extension. Particularly, the axial extension may be a main extension of the window. The main extension may be the largest extension the window has. The axial extension of the window may define a window axis. The window axis may be aligned with a main longitudinal axis of the dispensing device, when the display assembly is incorporated in the device.

In an embodiment, the display assembly comprises an indication member. The indication member may be provided to provide information to be displayed in the window, such as to a user of the dispensing device. The indication member may be moveable, preferably rotatable, relative to the body for changing the information displayed in the window. Accordingly, if the indication member is moved, the displayed information may change, thereby increasing the amount of information which is displayable in the window. A section of the indication member may be displayed through the window of the display assembly.

In an embodiment, the indication member comprises a plurality of pieces of information. The plurality of pieces of information may be provided by visual indicators, e.g. colours and/or indicia, such as digits, numbers, letters, words, written text, graphics, icons and/or combinations thereof. The pieces of information may be provided on a helical path along the indication member. The path may extend on the outer circumference of the indication member.

In an embodiment, the display assembly comprises a selection member. The selection member may be provided to select one of the pieces of information from the plurality of pieces of information provided by the indication member to be displayed in the window. The selection member may define a masking section and a non-masking section. The masking section may be configured and arranged to mask information provided by the indication member whereas the non-masking section is configured to transfer information from the indication member through the non-masking section. The masking section may be arranged to mask sections of the indication member, thereby preventing these sections to be displayed in the window. The indication member and the selection member may be arranged such that they overlap. The selection member expediently overlaps with the window.

Particularly, the masking section and the non-masking section may overlap with pieces of information provided on the indication member. Pieces of information which overlap with the non-masking section may be visible through the window, whereas pieces of information which overlap with the masking section preferably are not visible through the window as they are masked by the masking section.

The non-masking section and the window, particularly in conjunction with the masking section, may define a displayed section of the indication member. For this purpose, the non-masking section and the masking section may partially, preferably only partially, overlap with the window to define the displayed section of the indication member. As the masking section also partially overlaps with the window as well as the non-masking section, it is guaranteed that only a selected portion of the indication member is displayed through the window. The remaining portions of the indication member which would be visible in the window, as the window may have a significant axial extension, are masked by the masking section of the selection member.

The masking section may be formed by a body of the selection member. The selection member body may be translucent or opaque. A translucent body, even though light may penetrate through the body, does not permit to visually resolve information provided behind the translucent body. Accordingly, it is almost as suitable for a masking section as an opaque body. As an opaque body does not even hint that information is hidden behind that body, an opaque body may have slight advantages for the selection member body over a translucent body. The non-masking section may be formed by means of an opening or a cut-out of the selection member body.

In an embodiment, the selection member is movable, preferably rotatable, with respect to the body and/or with respect to the indication member. The selection member may be rotatable around a rotation axis. The rotation axis may be aligned with the axial extension direction of the window. The rotatability of the selection member with respect to the indication member facilitates selection of different pieces of information provided on the indication member by means of a selection member as there is relative rotation between the selection member and the indication member. As compared to an axial movement, a rotational movement is more space saving as no axial travel space has to be provided in the device for an axial travel of the selection member.

The cooperation of the selection element, the window and the indication member to define the displayed section of the indication member is particularly advantageous, as it facilitates provision of a very compact display assembly. Particularly, a display assembly may be provided where only rotational relative movement between the elements, particularly of the indication member and the selection member with respect to each other and/or with respect to the window, is necessary in order to change the displayed information. No axial displacement is required to do so. Accordingly, the design may be kept compact.

In an embodiment, the selection member and the indication member are coupled, particularly operatively coupled. The selection member and the indication member may be coupled such that the movement of one of these members is converted into movement of the other one of these members. For example, movement of the indication member, particularly rotational movement, with respect to the body may be converted into movement, particularly rotational movement, of the selection member with respect to the indication member. Alternatively or additionally, the selection member and the indication member may be coupled such that movement of the selection member, particularly rotational movement, with respect to the body is converted into movement, particularly rotational movement, of the indication member with respect to the selection member. Due to the coupling between the selection member and the indication member, the displayed section of the indication member may be displaced within the window.

The selection member and the indication member may be coupled such that the displayed section of the indication member is axially displaced within the window. This may be achieved even though the selection member and the indication member only rotate. More details will be explained further below.

In a dispensing device, the displayed section of the indication member may be displaced away from the dispensing end, particularly in the proximal direction, during the setting of the dose. During the dispensing action, the indication member may be displaced towards the dispensing end, particularly in the distal direction. The distance of the displayed section from a distal end of the window may give a hint on the size of the current dose. The distance may increase during setting of the dose and decrease during dispensing of the dose. Accordingly, by the position of the displayed section of the indication member within the window, a visual clue is given on the size of the currently set dose or the amount of substance remaining to be dispensed to complete the dispensing action for the whole dose.

In an embodiment, the non-masking section is arranged between two portions of the masking section, particular as seen along the window axis. One of the portions of the masking section is expediently arranged more distally than the other one. The portions may delimit the non-masking section. These portions of the masking section may be provided with different markings, for example with different colours. Accordingly, via the portions of the masking section which are displayed in the window, information can be transferred to the user. For example, that portion of the masking section which is closer to the dispensing end may be red and the portion which is further away from the dispensing end may be green. If the dose to be dispensed with the dispensing device is set the red length displayed in the window increases and the green length is reduced. When the dose is dispensed, the green length is again increased and, once it has reached its maximum length, it is indicated to the user that the dose has been successfully dispensed in its entirety. Of course the colours red and green could be substituted by other colours such as black and white. Additionally or alternatively, icons, graphics, materials, textures, and so on, which are provided on the masking section, may be used for transferring information to the user. The proximal and distal portions of the masking section between which the non-masking section is arranged may be differently marked.

In an embodiment, the selection member is configured such that, in each rotational position with respect to the window, only one continuous portion of the non-masking section overlaps with the window. Consequently, only one section of the indication member, e.g. the one overlapping with the non-masking section and the window, is displayed by the display assembly. Confusion regarding a plurality of displayed sections may be avoided in this way.

In an embodiment, the indication member is rotatable relative to the body.

In an embodiment, the indication member is axially constrained with respect to the body. The indication member may be locked against axial movement with respect to the body. Consequently, axial movement of the indication member may be prevented.

Thus, the selection member and the indication member may be prevented from axial movement with respect to the body and, accordingly with respect to the window. Relative rotation between window, indication member and/or selection member is expediently allowed.

In an embodiment, the selection member may be axially constrained with respect to the body. The selection member may be locked against axial movement with respect to the body. Consequently, axial movement of the selection member may be prevented.

In an embodiment, the indication member and the selection member are both rotatable around the rotation axis. This facilitates a particularly compact arrangement of the components of the display assembly.

In an embodiment, the non-masking section extends in the angular direction. The non-masking section may extend in the axial direction. Preferably, the non-masking section extends in the axial direction and the angular direction. The non-masking section may extend helically, particularly around the rotation axis. By means of the non-masking section which extends in the axial and in the angular direction, a relative rotation between the selection member and the indication member may be converted into an axial displacement of the displayed section of the indication member in a comparatively easy way. The helix of the non-masking section and the helix of the pieces of information on the indication member may have different pitches. The pitch of the non-masking section helix may be greater than the pitch of the pieces of information helix. The pitch of the respective helix may be constant as seen along the helix. For a sudden change of indication, the display assembly may be configured such that the non-masking section helix and the information helix are crossed, wherein one of said helices runs clockwise while the other one runs counter clockwise. For a less sudden change of indication, the display assembly may be configured such that said helices run in the same direction.

In an embodiment, the pieces of information which are provided on the indication member have a maximum axial extension along the indication member. The maximum axial extension may be given by the axial distance of the two ends of the path along which the pieces of information are provided along the indication member, such as a helical path. Expediently, the axial extension of the window and/or of the non-masking section is greater than or equal to the maximum axial extension. In this way, it can be ascertained that all of the pieces of information provided on the indication member may be displayed in the window, particularly without a required axial displacement of the indication member, of the window and/or of the selection member.

In an embodiment, the indication member is an indication sleeve. In an alternative or additional embodiment, the selection member is a selection sleeve. The indication sleeve may be retained in the selection sleeve.

In an embodiment, the indication member and the selection member are coupled such that they rotate in the same direction or in opposite directions, particularly when one of these members is moved with respect to the other one of these members.

In an embodiment, the display assembly comprises a display driver. The display driver may be coupled to either the indication member or the selection member to drive movement of the respective member with respect to the body. The display driver may be a part of a drive mechanism of the dispensing device, particularly of a drug delivery device. The drive mechanism may be operable to drive the dispensing action to dispense the substance from the device.

In an embodiment, the selection member and the indication member are coupled by a coupling member or a coupling mechanism. The coupling member may define a coupling member window. The coupling mechanism may, for example, be a spur gear train mechanism. By means of the coupling, movement of the indication member may be converted into movement of the selection member and vice versa.

The displayed section of the indication member displayed by the display assembly may be displayed through the coupling member window and the window. Accordingly, the coupling member window may further restrict the displayed section of the indication member in addition to the non-masking section, the masking section and, if applicable, the window. Alternatively or in addition to the restriction of the displayed section, the coupling member may also effect the coupling of the selection member and the indication member such that movement of one of them is converted into movement of the other one.

The coupling member may be threadedly coupled to, preferably threadedly engaged with, the indication member. Alternatively or additionally, the coupling member may be guided, particularly axially guided, with respect to or along the body and/or with respect to the window. Alternatively or additionally, the coupling member may be guided along the non-masking section of the selection member. The axial guiding with respect to the window restricts possible movement of the coupling member to axial movement with respect to the body. This axial movement, due to its coupling to the non-masking section and/or the indication member, would result in rotational movements of these members if the coupling member was moved axially relative to the indication member or the selection member.

If the indication member is driven to change the information displayed by the display assembly, rotation of the indication member with respect to the body may, on account of the threaded coupling, be converted into axial movement of the coupling member with respect to the body and this axial movement, again, may be converted into rotational movement of the selection member on account of the coupling member being guided along the non-masking section of the selection member. If the selection member is driven, rotational movement of the selection member is converted into axial movement of the coupling member, which is again converted into rotational movement of the indication member.

In an embodiment, the window is formed by an opening in the body. The opening may be covered by a window member connected to the body, particularly preferably a window insert. Alternatively or additionally, the opening may be covered by a label, preferably a label which is transparent at least in the portion overlapping the window. The label may, e.g. compared to the window member, be more flexible. The label may be applied to the body by an adhesive, for example. Particularly drug delivery devices, but also other dispensing devices, often require a label to be applied to their outside, the label providing information about the device, such as about the substance to be dispensed, the sell-by date and so on. The label or the window member is expediently transparent so as to permit the information which is displayed through the window to be retrieved by the user.

The label may have to be present in the device anyway for regulatory reasons. The use of the same label for covering the opening in the body is beneficial for the display assembly as no separate member has to be provided.

Due to the covered opening, the interior of the display assembly may be sealed with respect to the environment. Accordingly, debris from the environment, such as dirt, is prevented from entering through the window and can thus not impair the readability of the information displayed in the window or the functionality of the display assembly.

In an embodiment, the dispensing device is a drug delivery device and the body is a housing of the drug delivery device. The display assembly may provide a dose display mechanism. The dose display mechanism may be provided to display the size of the dose, which is set to be dispensed by the drug delivery device, to a user through the window.

In a particular advantageous embodiment, a display assembly is provided, comprising:
- a body defining a window having an axial extension,
- an indication member for providing information to be displayed in the window, wherein the indication member is movable relative to the body for changing the information displayed in the window,
- a selection member, wherein
  - the selection member defines a masking section and a non-masking section,
  - the selection member is rotatable around a rotation axis with respect to the body and with respect to the indication member,
  - the non-masking section and the masking section partially overlap with the window to define a displayed section of the indication member, and
  - wherein
the selection member and the indication member are coupled such that:
a) movement of the indication member with respect to the body is converted into rotational movement of the selection member with respect to the indication member and/or
b) rotational movement of the selection member with respect to the body is converted into movement of the indication member with respect to the selection member, wherein in a) and b) the displayed section of the indication member is axially displaced within the window.

The proposed display assembly relies on rotational movement of the selection member to select the information displayed by the indication member in the window.

Conventional drug delivery devices often utilize a threaded number sleeve as an indication member which is, when a dose is set, axially displayed with respect to the housing of the device, the distance of displacement being proportional to the size of the set dose. Accordingly, the length of the device in the "dose set" state is increased in this way. The present display assembly provides for a display assembly which does not necessarily increase the length of the dispensing device as, due to the rotating selection member, it enables the selection of a displayed piece of information without requiring axial displacement of the indication member.

Features described above in conjunction with different aspects or embodiments may be combined with each other and with features described further below.

Further features and advantages of the present disclosure will become apparent from the description of the exemplary embodiment in conjunction with the figures. Although the display assembly is described below in conjunction with a drug delivery device, it is readily apparent from the disclosure above that the dispensing device can also be a non-drug delivery medical device or a non-medical device such as the devices set forth further above. Consequently, features disclosed below for the drug delivery device may also relate to a dispensing device in general, be it a medical or a non-medical one.

Figure 1:
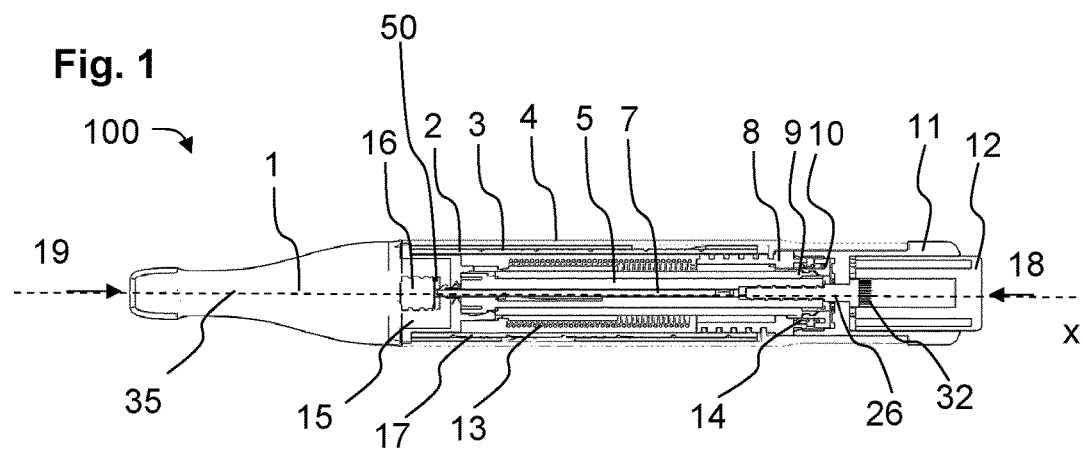
FIG. 1 shows a sectional side view of a drug delivery device comprising a drive mechanism.

Like elements, elements of the same kind and identically acting elements may be provided with the same reference numerals in the figures. Additionally, the figures may not be true to scale. Rather, certain features may be depicted in an exaggerated fashion for better illustration of important principles.

FIG. 1 shows a drug delivery device 100 comprising a drive assembly. A plurality of components and functionalities which are described herein relate to said drive assembly. The drive assembly, in turn, comprises a main drive mechanism and an auxiliary drive mechanism which are described further below.

The drug delivery device 100 comprises a proximal end 18 and a distal end 19. The drug delivery device 100 further comprises a main longitudinal axis x which is disposed between the proximal end 18 and the distal end 19. The drug delivery device 100 further comprises a housing 4. The housing 4 may house or retain further components of the drug delivery device 100. The housing 4 may be a body. The drug delivery device 100 further comprises a window 17. The window 17 may comprise an elongate shape with a longitudinal axis being aligned with the longitudinal axis x. The drug delivery device 100 further comprises an indication member 2 which provides pieces of information to be displayed through the window 17 of the drug delivery device 100. The indication member 2 may be an indication sleeve. Said information to be displayed may pertain to the size of a dose of a drug 35 to be dispensed from the drug delivery device 100. Therefore, the indication member 2 may comprise indicia (cf. 28 in FIG. 7) which indicate units or quantities of drug 35. The drug delivery device 100 further comprises a selection member 3 which may be a selection sleeve. The selection member 3 may mask information provided by the indication member 2 to be displayed through the window 17. The indication member 2 and the selection member 3, preferably, comprise an elongate shape. Preferably, the indication member 2 and the selection member 3 are rotatable around the longitudinal axis x with respect to the housing 4. A longitudinal axis of the indication member 2 and a longitudinal axis of the selection member 3 are preferably aligned with the longitudinal axis x. Said components are further preferably not axially moveable with respect to the housing.

The drug delivery device 100 further comprises a cartridge 1 containing the drug 35. The cartridge may be a 1.5 ml cartridge or a 3.0 ml cartridge. The cartridge may also contain different volumes of drug. A plunger 16 is retained at the proximal end of the cartridge 1. In the depicted situation, drug 35 has not yet been dispensed from the drug delivery device 100. The drug delivery device 100 further comprises a drive member 5 which is provisioned to drive the piston rod 7 during a dispensing action, i.e. when a set dose of drug 35 is dispensed from the drug delivery device 100. The drive member 5 comprises an elongate shape with a longitudinal axis being aligned with the longitudinal axis x. The drive member 5 is preferably rotatable in a first direction with respect to the housing 4.

The drug delivery device 100 further comprises a piston rod 7. The piston rod 7 comprises a distal termination 50 which may be rotatable with respect to the piston rod 7 and which is preferably arranged axially next to the plunger 16. The drive member 5 is rotationally locked with respect to the piston rod 7. Both components comprise an elongate shape with a longitudinal axis preferably aligned to the longitudinal axis x. Preferably, the drive member 5 is rotatable but axially constrained with respect to the housing 4. The piston rod 7 is threadedly engaged to a nut member 15 which is fixed to the housing 4 or unitarily formed by the housing 4. To this effect, the piston rod comprises an outer thread 36 (cf. FIG. 10) matching with an inner thread (not explicitly indicated) of the nut member 15. During dispensing of a set dose of drug 35, the drive member 5 preferably interacts with the piston rod 7 such that the piston rod 7 is moved distally due to the threaded engagement with the nut member 15. Consequently, the plunger 16 is advanced with respect to the cartridge 1 in the distal direction. Thereby, drug 35 is preferably dispensed from the drug delivery device 100.

The drug delivery device 100 may further comprise a needle or a needle assembly (not explicitly indicated). Said needle or needle assembly is preferably fluidly connected to the cartridge 1 such that during a dispensing action, drug 35 may be dispensed through the needle or the needle assembly.

The drug delivery device 100 may further comprise a cap (not shown) covering e.g. the distal end 19 and/or a needle hub to which the needle may be mounted. The cap may be provisioned to protect the distal end 19 of the drug delivery device 100 from contamination.

The drug delivery device 100 further comprises a ratchet member 8 comprising a sleeve-like shape. The ratchet member 8 comprises an outer thread 31 by which it is threadedly engaged to the housing 4. The drug delivery device 100 further comprises a resilient member 13. The resilient member 13 is a torsion spring. The resilient member is preferably connected to the housing 4 and to a distal end of the ratchet member 8. By a rotation (cf. second direction below and 39 in FIG. 2) of the ratchet member 8 with respect to the housing 4, the resilient member 13 is biased. The ratchet member 8 is furthermore coupled to the housing 4 via a releasable uni-directional coupling.

Due to its threaded engagement with the housing 4, the ratchet member 8 ratchets the resilient member 13 such that spring energy of the resilient member 13 is stored during a setting action, i.e. when, the setting mode of operation, a dose of drug 35 is set. The ratchet member 8 may prevent a relaxation of the resilient member 13 when a dose is set. The resilient member 13 preferably relates to the main drive mechanism of the drive assembly. Particularly, the resilient member 13 may drive the main drive mechanism.

The ratchet member 8 may be a display driver which drives the indication member 2 during an operation (e.g. a setting or dispensing action) of the drive assembly. To this effect, the indication member 2 may rotationally locked with respect to the ratchet member 8 via an axial rib 38.

The drug delivery device 100 further comprises a dose member 9 which is rotationally locked with respect to the drive member 5. The dose member 9 comprises an elongate shape with a longitudinal axis aligned with the longitudinal axis x. Preferably, the dose member 9 is axially moveable with respect to the housing 4. The dose member 9 is provisioned to transfer a torque or rotation to the drive member 5 during an operation of the drug delivery device 100. Particularly, in a dispensing mode of operation, the dose member 9 rotates along with the drive member 5 in a first direction with respect to the housing 4.

The drug delivery device 100 further comprises an actuation member 12 which is arranged at a proximal end 18 of the drug delivery device 100. The actuation member 12 is axially movable with respect to the housing 4. Particularly, a user can depress the actuation member 12 with respect to the housing 4. The actuation member 12 may be a button. When the actuation member 12 is moved distally with respect to the housing such as depressed by the user, a drive assembly of the drug delivery device 100 is preferably switched from the setting mode to the dispensing mode of operation.

The drug delivery device 100 further comprises a dose setting member 11 by which the user of the drug delivery device 100 may set a dose of drug 35 which is to be dispensed from the drug delivery device 100. To this effect, the user may manually rotate the dose setting member 11 in the second direction being opposite to the first direction with respect to the housing 4. In the setting mode of operation, the dose setting member 11 is rotationally locked with respect to the ratchet member 8.

The actuation member 12 is partially retained within the dose setting member 11. The actuation member 12 is rotationally locked but axially moveable with respect to the dose setting member 11.

The drug delivery device 100 further comprises an auxiliary drive member 26 forming part of the auxiliary drive mechanism. The auxiliary drive member has an elongate shape with a longitudinal axis being aligned with the longitudinal axis x. The drive assembly is configured such that when, in the setting mode of operation, a dose is set, the auxiliary drive member 26 is rotated in the second direction with respect to the drive member 5. In the dispensing mode of operation, the auxiliary drive member preferably mechanically assist the rotation of the drive member 5, whereby the piston rod 7 is moved distally with respect to the housing 4 due to the mentioned thread engagement with the nut member 15. To this effect, the drive member 5 is threadedly engaged to the auxiliary drive member 26.

When the actuation member 12 is depressed, the rotational coupling between the dose setting member 11 and the ratchet member 8 is released.

The actuation member 12 may have at least one actuation pin 49 which interacts with the clutch element 10 to move it axially relative to the dose setting member 11, therebys disengaging the proximal teeth 51 from the distal teeth 53.

The drug delivery device 100 further comprises a clutch element 10 and a clutch spring 14. The clutch spring 14 is retained between the ratchet member 8 and the clutch element 10, thereby tending to move the ratchet member 8 and the clutch element 10 away from each other. When in the setting mode of operation, the actuation member 12 is moved proximally with respect to the housing 4, and the clutch element 10 is moved distally with respect to the housing 4 thereby disengaging the releasable unidirectional coupling.

Figure 2:
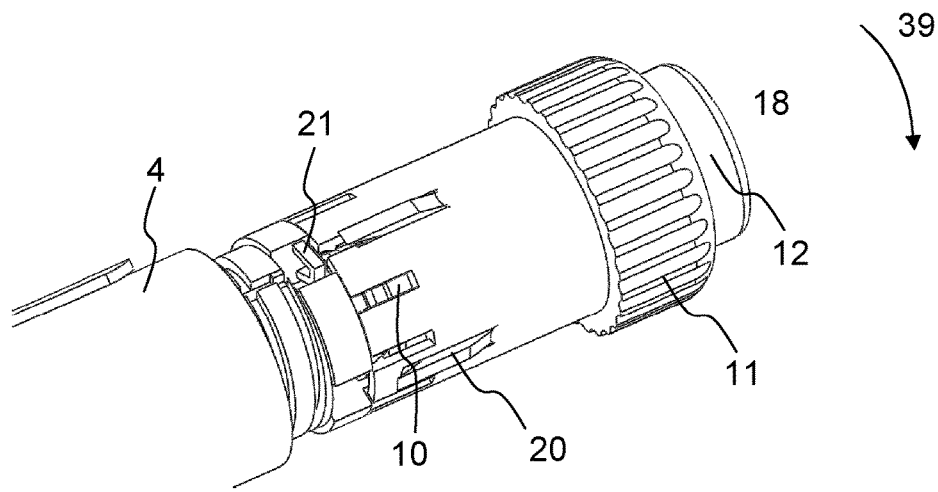
FIG. 2 shows a perspective view of parts of a proximal end of the drug delivery device.

FIG. 2 shows parts of the proximal end 18 of the drug delivery device 100 without the housing 4. It is shown that the ratchet member 8 comprises ratchet features 21 (only one shown in FIG. 2) which—when assembled in the drug delivery device 100 (cf. FIG. 1)—engages teeth 22 of the housing 4 (cf. FIG. 3), thereby forming the releasable uni-directional coupling between the ratchet member 8 and the housing 4. Furthermore, the actuation member 12 comprises actuation features 20. The drive assembly is configured such that when, in the setting mode of operation, the actuation member 12 is moved distally with respect to the housing 4, the actuation features 20 are pushed radially outwards through slots (not explicitly indicated) of dose setting member 11. Consequently, the actuation features 20 engage with the teeth 22 on the inside of the housing 4 (cf. FIG. 3). Thereby, the actuation member 12 rotationally locks the dose setting member with respect to the housing 4.

During a setting action, the ratchet feature 21 may slide over teeth of the teeth 22. Thereby, the ratchet feature 21 may be slightly deflected inwards until it has passed the respective tooth. Preferably, the teeth 22 is configured such that—provided the releasable uni-directional coupling is engaged—the ratchet member 8 can only be rotated in one direction with respect to the housing 4. Preferably, the movement of the ratchet member 8 corresponding to that of the ratchet feature 21 passing one tooth of the teeth 22 relates to the setting of a minimum settable dose of drug 35.

The drive assembly is configured such that in the setting mode of operation, the releasable uni-directional coupling is established and, in the dispensing mode of operation, the releasable uni-directional coupling is disengaged and the ratchet member 8 rotates in the first direction with respect to the housing 4 such that also the drive member 5 is rotated in the first direction with respect to the housing 4. The arrow 39 indicates the second direction according to which the dose setting member 11 is rotated with respect to the housing 4 during a setting action, whereby a dose of drug 35 of the drug delivery device 100 is set.

Figure 3:
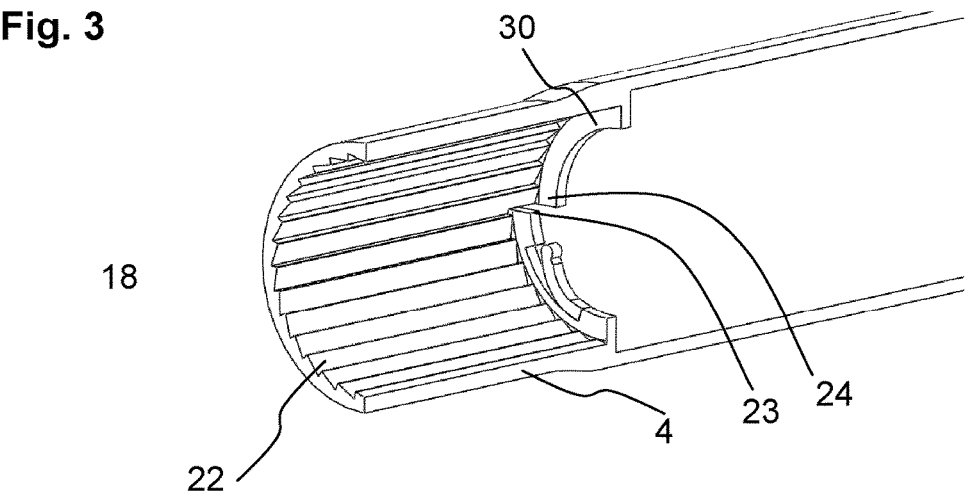
FIG. 3 shows a sectional perspective view of a proximal end of a housing of the drug delivery device.

FIG. 3 shows a cross-section of the proximal end 18 of the housing 4. One can observe the teeth 22 at the inside of the housing 4. The teeth 22 interact with the ratchet feature 21, in order to form the releasable unidirectional coupling, as mentioned above.

When, in the setting mode of operation, the actuation button 12 is depressed with respect to the housing, the ratchet features 21 are pulled radially inwards by a finger (not shown) on the clutch element 10, allowing the ratchet member 8 to rotate due to a driving force of the biased resilient member 13. The ratchet features 21 may take the form of a loop and the finger on the clutch element 10 may interact with the inner surface of said loop, thus pulling the ratchet features 21 radially inwards and disengaging them from the teeth 22.

The housing 4 further comprises a setting stop 23 and a dispensing stop 24. These components prevent under certain conditions a rotation of the ratchet member 8 with respect to the housing 4 in the proximal and in the distal direction, respectively. Said stops may engage with corresponding stops on the ratchet member 8, respectively. A corresponding setting stop may, e.g. be arranged at a proximal end of the outer thread 31 of the ratchet member 8 and a corresponding dispensing stop may be arranged at a distal end of the outer thread 31. Thus, between certain limits, the ratchet member 8 is rotationally moveable with respect to the housing 4.

Figure 4:
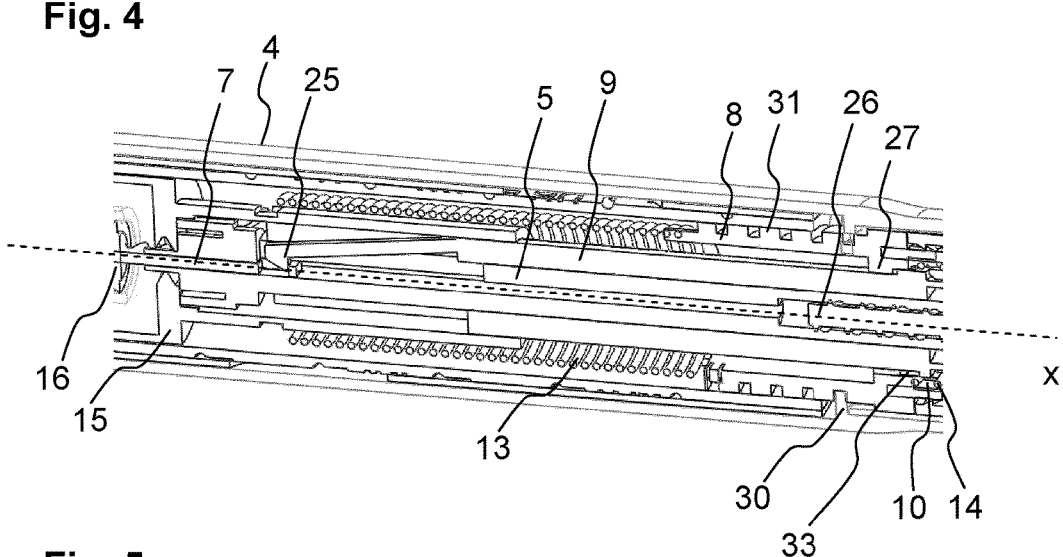
FIG. 4 shows a sectional view of inner components of the drug delivery device.

FIG. 4 shows inner components of the drug delivery device 100. Particularly, a last dose feature 25 of the dose member 9 is shown which is arranged to engage a piston rod feature 43 of the piston rod 7. During a setting action, the dose member 9 preferably rotates in a second direction with respect to the housing 4 and with respect to the drive member 5. When, in the setting mode of operation— whereby the dose member 9 moves axially away from the distal end 19—the maximum settable dose of drug 35 is reached. In the setting mode of operation, the axial distance by which the dose member 9 may be moved proximally is equal or less than the axial distance between the last dose feature 25 and the piston rod feature 43. The axial distance between the piston rod feature 43 and the last dose feature 25 is indicative for an amount of drug 35 remaining to be dispensed from the drug delivery device 100. When the last dose feature 43 and the piston rod feature 25 are engaged, the dose member 9 is prevented from being moved further proximally. The last dose feature 25 prevents the user from setting a dose greater than the one corresponding to the available volume in the cartridge 1.

The drive assembly comprises a drive coupling being configured such that in the setting mode of operation, the ratchet member 8 is free to rotate with respect to the dose member 9. In this situation, the drive coupling is preferably disengaged. The drive coupling is further configured such that the dispensing mode of operation, the ratchet member 8 is rotationally locked with respect to the dose member 9 such that, during a dispensing action, the dose member is rotated in the first direction with respect to the housing 4. In this situation, the drive coupling is, preferably engaged.

In order to achieve the drive coupling, the ratchet member 8 comprises ratchet splines 27 which engage corresponding dose member splines 33 of the dose member 9 when the actuation member 12 is depressed.

Figure 5:
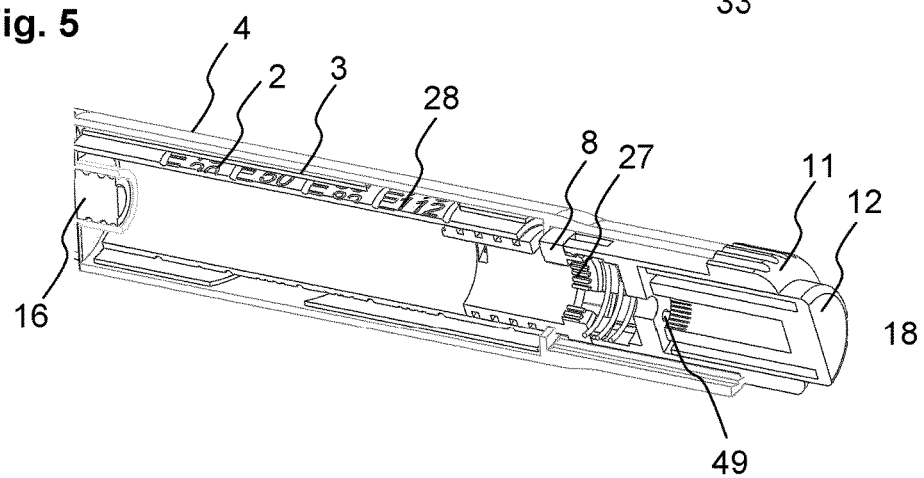
FIG. 5 shows a sectional perspective view of inner components of the drug delivery device.

FIG. 5 shows selected components of the drug delivery device 100 by means of a sectional perspective view. In the depicted situation, the actuation member 12 is not pressed such that the setting mode of operation is indicated. Particularly, the ratchet splines 27 of the ratchet member 8 are shown which are configured to engage the dose member splines 33 when it is switched to the dispensing mode of operation. The actuation member 12 comprises an actuation pin 49 by which the actuation member 12 and the dose setting member 11 are rotationally locked. When the actuation member 12 is pressed, the actuation pin 49 pushes the clutch element 10 in the distal direction, thereby distally displacing the clutch element 10 such that ratchet splines 27 disengage the dose member splines 33 of the dose member 9 and the releasable uni-directional coupling is released.

Figure 6:
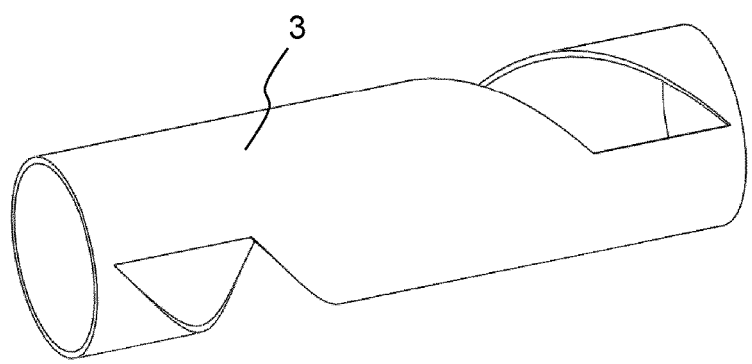
FIG. 6 shows a perspective view of a selection member of the drug delivery device.
Figure 8:
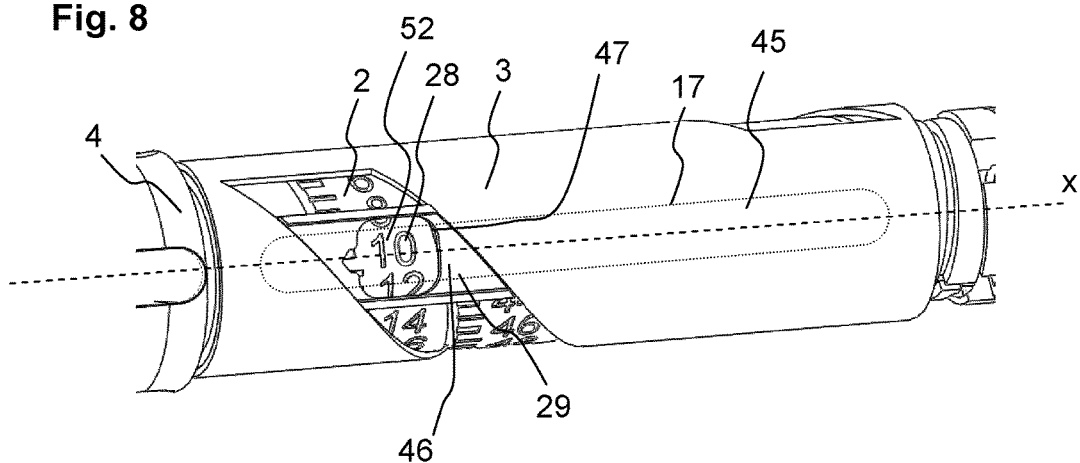
FIG. 8 shows a perspective view of a display assembly of the drug delivery device.

FIG. 6 shows the selection member 3 which forms part of and display assembly of the drug delivery device 100 (cf. FIG. 8). The selection member 3 is a selection sleeve comprising a non-continuous helical cut-out.

Figure 7:
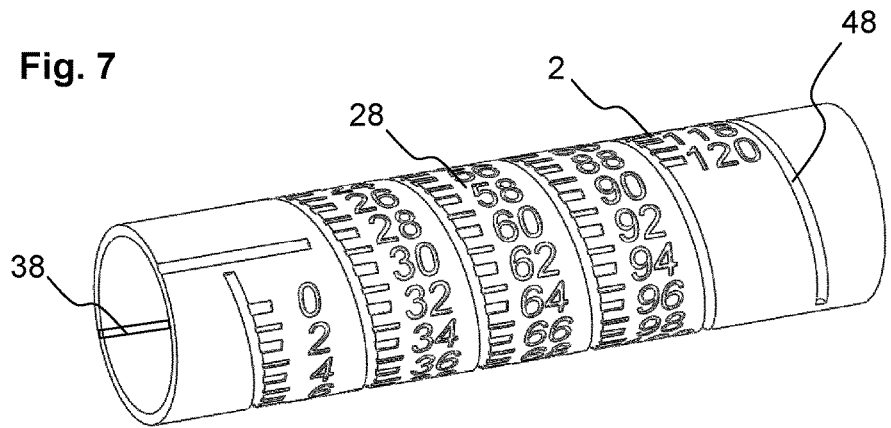
FIG. 7 shows a perspective view of an indication member of the drug delivery device.

FIG. 7 shows in the indication member 2 further comprising indicia 28. The indication member 2, as well forms a part of the mentioned display assembly of FIG. 8. The indicia 28 may comprise dose numbers indicating quantities or units of drug 35 to be dispensed from the drug delivery device 100. The indicia 28 may be arranged helically around the circumference of the indication member 2. The indicia may extend for example from "zero" at a distal end of the indication member 2 to the maximum allowable dose, for example "120" at a proximal end of indication member 2. The drug delivery device 100 further comprises a coupling member 29. The indication member 2 further comprises an indication member thread 48 to which a coupling member 29 (cf. FIG. 8) may be threadedly engaged. The coupling member 29 may be a sliding window sliding axially along the window 17. The indication member 2 further comprises an axial rib 38 by which the indication member 2 may be rotationally locked with respect to the ratchet member 8. Therefore, the ratchet member 8 may comprise a corresponding notch (not explicitly indicated) engaging the axial rib 38.

FIG. 8 shows at least parts of the display assembly of the drug delivery device 100 comprising the indication member 2, the selection member 3 and the coupling member 29. The coupling member 29 is threadedly engaged to the indication member thread 48. The coupling member 29 is further rotationally locked but axially moveable with respect to the housing 4. When, during an operation of the drug delivery device 100, the indication member 2 is rotated by way of a rotation of the ratchet member 8, the coupling member 29 is moved axially with respect to the housing, thereby driving or rotating the selection member 3 with respect to the indication member 2. Said rotation of the selection member 3 occurs in the same direction in which also the indication member 2 has been rotated previously.

At rest or in an initial position, the display assembly preferably displays "0" or an equivalent marking to show that no dose has been set.

An application of the display assembly is not bound to drug delivery devices but may relate to any conceivable delivery device or further applications.

The selection member 3 defines a masking section 45 and a non-masking section 46. A non-masking section 46 and the masking section 45 partially overlap with the window 17 which is indicated dashed in FIG. 8. A movement of the indication member 2 with respect to the housing 4 is converted into rotational movement of the selection member 3 with respect to the indication member 2.

The display assembly may be configured such that the indication member 2 and the selection member 3 are coupled such that they rotate in the same direction or in opposite directions, particularly when one of these members is moved with respect to the other one of these members.

The coupling member 29 comprises a coupling member window 47. Due to the interaction of the indication member, the selection member and the coupling member, only a limited amount of information is displayed to the user, thus preventing confusion during an operation of the drug delivery device 100. The masking section 45 may be formed by a body of the selection member 3.

The selection member 3 and the indication member 2 are preferably coupled such that movement of the indication member with respect to the housing 4 is converted into rotational movement of the selection member 3 with respect to the indication member 2.

Alternatively, the selection member 3 and the indication member 2 are preferably coupled such that rotational movement of the selection member 3 with respect to the housing 4 is converted into movement of the indication member 2 with respect to the selection member 3.

The non-masking section 46 and the window 17, particularly in conjunction with the masking section 45, may define a displayed section 52 of the indication member 2. For this purpose, the non-masking section 46 and the masking section 45 may partially, preferably only partially, overlap with the window 17 to define the displayed section 52 of the indication member 2. As the masking section 45 also partially overlaps with the window 17 as well as the non-masking section 46, it is guaranteed that only a selected portion of the indication member 2 is displayed through the window 17. The remaining portions of the indication member 2 which would be visible in the window 17, as the window 17 may have a significant axial extension, are masked by the masking section 45 of the selection member 3.

The displayed section 52 of the indication member 2 may be axially displaced within the window 17.

Preferably, the non-masking section 46 is arranged between two portions of the masking section 45, particular as seen along the window axis. One of the portions of the masking section 45 is expediently arranged more distally than the other one. The portions may delimit the non-masking section 46. These portions of the masking section 45 may be provided with different markings, for example with different colours.

In the situation depicted in FIG. 8, the number "10" is displayed through the coupling member window 47 and the window 17. The window 17 may be covered either by a window insert connected to the body or by a label, preferably a transparent label. Said body insert may be a magnifying insert and shaped like a lens in order to magnify or increase the apparent size of the indicia 28 on the indication member 2.

As an alternative to the coupling member, the selection member 3 could also be driven relative to the indication member 2 by, e.g., a spur gear train.

As mentioned above, the display assembly is configured such that the indication member 2 and the selection member 3 preferably do not move axially with respect to the housing. This provides the advantage of a compact embodiment of the drug delivery device 100, as compared to devices which require e.g. large axial displacements of the respective indication sleeves. In the presented concept, the geometry of the indicia is not directly tied to the geometry of the drive assembly. Thereby, the indicia may be embodied comparably large.

Another advantage of the described display assembly relates to the fact that the position of the coupling member window 47 moves axially when the device is operated. This gives particularly a visual cue to the user that the set dose is increased during a setting action and the dose to be dispensed is decreased during a dispensing action.

The indicia 28 do not necessarily comprise numbers. The indicia could also comprise visual indicators, e.g. colours, digits, numbers, letters, words, written text, graphics, icons and/or combinations thereof. In addition to the information provided by the indicia 28, an external face of the indication member 2 could be coloured, e.g. red at in a distal region and green in a proximal region. The indication member 2 may be configured such that when the set dose is increased, the length of the red region which is visible through the window 17 is increased and the length of the green region is reduced. Said colours may also be varied or changed.

Figure 9:
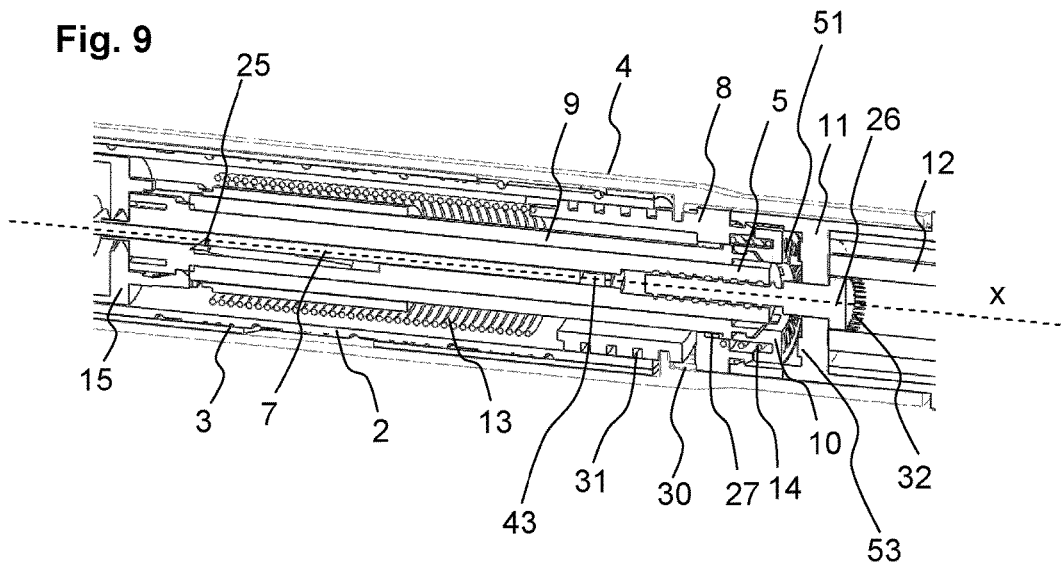
FIG. 9 shows a sectional view of inner components of the drug delivery device.

FIG. 9 shows inner components of the drug delivery device 100 in the dispensing mode of operation, wherein the actuation member 12 is depressed, i.e. moved distally with respect to the housing 4. When, originating from the setting mode of operation, the actuation member 12 is moved distally with respect to the housing 4, the actuation member 12 rotationally locks in the auxiliary drive member 26 via actuation member splines 32. The clutch element 10 may comprise proximal teeth 51 which—in the setting mode of operation—engage distal teeth 53 of the dose setting member 11 by way of the clutch spring 14. Thus, setting mode of operation, the dose setting member 11 and the clutch element 10 are rotationally locked by the proximal teeth 51 and the distal teeth 53.

For the rotational locking between the dose setting member 11 and the ratchet member 8, the dose setting member 11 has distal teeth 53 which engage with proximal teeth 51 provided by the clutch element 10. The clutch element 10 may have a dose setting finger (not explicitly indicated) which is configured to engage the ratchet member 8.

In the setting mode of operation, the ratchet member 8 is free to rotate with respect to the dose member 9. The ratchet member 8 is further rotationally locked with respect to the dose setting member 11. During setting of a dose, the clutch element 10 rotates along with the ratchet member 8 and the dose setting member 11. During delivery of a dose, the clutch element 10 rotates with the ratchet member 8 without rotating with the dose setting member 11 which is rotationally fixed with respect to the housing 4. When a user rotates the dose setting member 11 in order to set a dose, the ratchet member 8 rotates in the second direction with respect to the housing 4 and simultaneously moves proximally with respect to the housing 4 due to the threaded engagement thereto (cf. threads 30 and 31). Thereby, the resilient member 13 is biased and a relaxation of the resilient member or a back rotation is prevented by the releasable uni-directional coupling between the ratchet member 8 and the housing 4.

When the user then presses the actuation member 12 with respect to the housing 4, it may have a small travel of, e.g. 1 mm in which no action takes place. When the actuation member 12 has been moved by the full distance (cf. FIG. 1) in the distal direction with respect to the housing 4, it is switched from the setting mode to the dispensing mode of operation, as mentioned above. Moreover, the releasable uni-directional coupling is released and the ratchet member 8 is now free to rotate with respect to the housing 4. Simultaneously, the ratchet member 8 is rotationally locked to the dose member 9 via the mentioned drive coupling. Moreover the dose setting member 11 is rotationally locked with respect to the housing 4 via the actuation features 20 of the actuation member 12. Consequently, the spring energy of the resilient member 13 which is stored during setting of the dose is exerted to the ratchet member 8 which, thus, rotates in the first direction with respect to the housing 4. As said rotation of the ratchet member 8 being rotationally locked with respect to the dose member 9 is further transferred to drive member 5 and the piston rod 7, said piston rod 7 rotates in the first direction. Due to the threaded engagement of the piston rod 7 with the nut member 15, the plunger 16 is thus advanced within the cartridge 1 in order to dispense the set dose of drug 35 from the drug delivery device 100.

Additionally, the pressure exerted by the user to the actuation member 12 may be directly exerted to the drive member 5 via the auxiliary drive member 26. When the user depresses the actuation member 12, the auxiliary drive member 26 is rotationally locked with respect to the actuation member 12 by actuation member splines 32 and pressure is transferred or converted into a rotation of the drive member 5 with respect to the housing 4 due to the threaded engagement of the auxiliary drive member 26 and the drive member 5. Therefore, the stronger the user presses the actuation member 12, the more torque is exerted to the drive member 5 and the faster the piston rod 7 will rotate, thereby assisting the advancement of the plunger 16 in the cartridge 1 during the dispensing action. This functionality characterizes the auxiliary drive mechanism. When or before the actuation member 12 abuts a proximal face of the dose setting member 9 during the axial travel of the actuation member 12, the auxiliary drive member 26 may abut an actuation stop (not explicitly indicated) such that an axial force may be exerted to the auxiliary drive member 26.

The problems with spring-driven drug delivery devices are that the user has no control over the speed of dispensing or injection and the user has little haptic feedback of the injecting or dispensing progress because the thumb by which the actuation member 12 is preferably actuated according to the presented concept, does not move. The presented concept may be suitable for the dispensing of 120 units of insulin formulation or a different drug, whereby the user is allowed to control the dispensing and whereby haptic feedback is provided from the movement of the actuation member 12.

The end of a dispensing or injection action may be indicated to the user by a feature which e.g. provides for an acoustic feedback when two components move relative to one another at the end of the dispensing action. If an acoustic feedback is required, every time the display assembly displays zero doses, then, the mentioned feature could be provided by the indication member, the selection member, the coupling member or the ratchet member, for example. If the acoustic feedback is required only once at the end of a dispensing action (and not during a setting action), said feature could be provided at the drive member or the dose member such that a relative movement between these components provides the acoustic feedback.

When, once the actuation member 12 has been pressed, the axial or distal force on the actuation member 12 is removed, the actuation member 12 returns to its initial axial position relative to the dose setting member 11. Thereby, the ratchet member 8 is again engaged with the housing 4 via the releasable uni-directional coupling, thus preventing further dispensing. The actuation features 20 are furthermore pulled radially inwards such that the dose setting member 11 is rotatable with respect to the housing 4 again.

Figure 10:
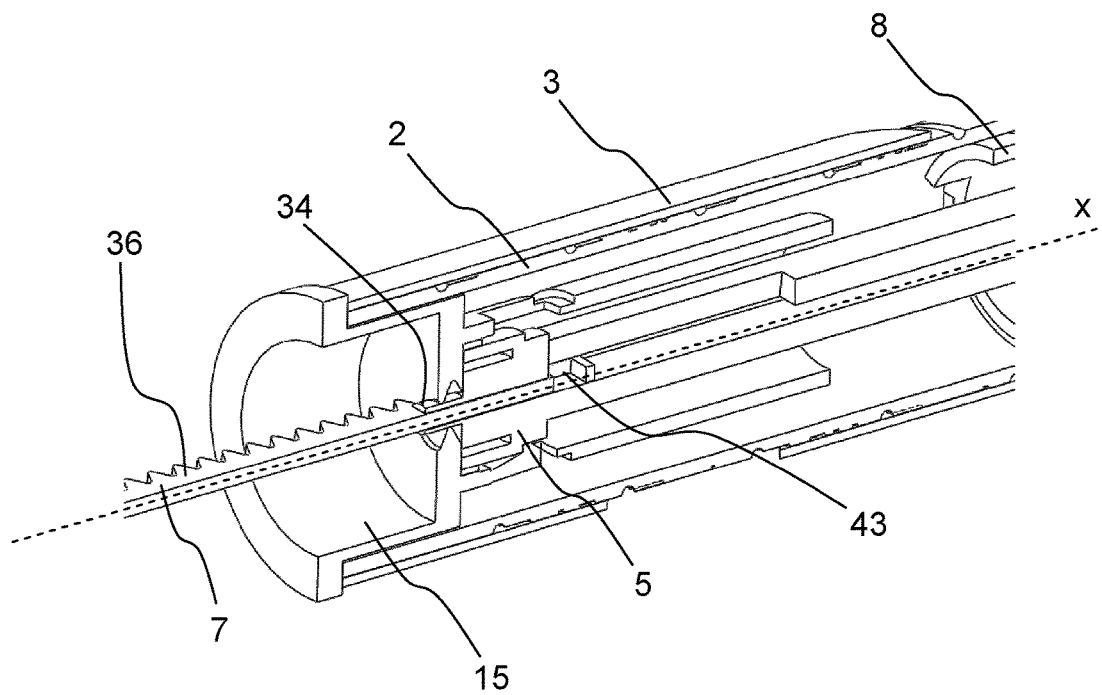
FIG. 10 shows a sectional perspective view of inner components of the drug delivery device.

FIG. 10 shows inner components of the drug delivery device 100 by means of a respective sectional view. Particularly, FIG. 10 shows the piston rod 7 comprising a thread 36 in greater detail. The piston rod 7 and also further components of the drive assembly or the drug delivery device 100 are shown sectional, only. One can see that the thread 36 does not extend along the whole circumference of the piston rod 7. Instead, the thread 36 is only formed or embodied on opposing sides of piston rod 7 (only one side is shown due to the sectional view). According to this embodiment, the piston rod 7 may be formed from sheet metal. As compared to e.g. piston rods made from moulded thermoplastics, the use of sheet metal allows smaller tolerances. Thermoplastics, on the other hand, are liable to creep if a load is provided on them for extended durations. Furthermore, the magnitude of force transferred through plastic plunger rods may be limited by the material strength. Indeed, the high density of steel can lead to breakages during drop testing. The reduced mass of a plunger rod manufactured from sheet metal compared with a conventional plunger rod, however, should reduce the number and severity of failures e.g. in drop testing.

Moreover, the reduced mass accompanied by the use of sheet metal allows material cost savings. Additionally, the processes involved in the manufacture of sheet metal are typically less time-consuming and, therefore, cheaper. Additionally, less waste of material is created, as compared to conventional machining processes.

Two or more plunger rods manufactured from sheet metal could be stacked to create, e.g. a "conventional" bulk manufactured plunger rod. For example, two or more plunger rods which are fabricated from sheet metal may be axially sprung relative to one another such that they provide an anti-backlash functionality.

The drive member 5 further comprises a drive member support 34, thus supporting the piston rod 7 at lateral sides of the piston rod 7 not comprising the thread 36 within a bearing of the nut member 15. Due to the support 34, the drive member 5 cannot move away from the main axis of the drug delivery device 100 and radial movement of the piston rod 7 is prevented.

The drug delivery device 100 may need to be primed, i.e. the act of preparing the device for the first use. Priming may relate to setting and delivering one or more small doses into air so that any play, clearances or tolerances in the drug delivery device 100 are removed and the components are brought into suitable compression or tension. After first use, and before each subsequent use, a 'safety shot' may be dispensed into air to ensure that the needle is not blocked.

The drug delivery device 100 may be used to dispense or inject a drug, a substance such as a liquid medicament. The steps the user may have to carry out in this respect comprise the removal of the cap, the fitting of the needle, the dialing or setting of a priming dose—which may comprise two units of insulin formulation—by rotating the dose setting member 11, the dispensing of the set priming dose by pressing the actuation button 12, the setting of a dose which is actually to be dispensed for the drug delivery device 100 by rotating the dose setting member 11, inserting the needle, dispensing the set dose by pressing the actuation member 12 and the removal of the needle from the device and replacing the cap to the drug delivery device 100.

Actually, layout, function and number of components of the drive assembly may differ from the illustrations presented in the figures.

The drug delivery device 100 may be disposable such that the cartridge 1 cannot be replaced. Alternatively, the drug delivery device 100 may be reusable, wherein the cartridge 1 may be replaced or removed from a cartridge holder of the drug delivery device 100 or the drug delivery device 100. Furthermore, the drive assembly may be configured such that the piston rod 7 is resettable which may be expedient if the drug delivery device 100 is reusable.

The display assembly is preferably configured such that when a minimum settable dose is set, the spring energy of the resilient member 13 stored during the setting action is sufficient to deliver said minimal dose.

Although not explicitly indicated and described, the drive assembly may be configured such that a set dose may be changed or decreased, e.g. by rotating the dose setting member 11 in the first direction once a dose has been set. To this effect, the teeth 22 and the ratchet features 21 may be configured accordingly. In this case, the releasable unidirectional coupling is to be replaced by, e.g. a releasable bi-directional coupling.

A "hold time" is the period from when the drive mechanism and/or the auxiliary drive mechanism has stopped moving—this may be the case when the display assembly displays "0"—to when the dose is fully dispensed. The hold time is required, as, if a user dispenses the drug too fast, it takes some time until the elasticity of components of the drive assembly equilibrate such that the correct volume of drug 35 is delivered.

Motor-driven drug delivery devices often cause problems, as the motors are expensive, the motors are heavy, the motors require a power supply such as batteries which add further cost, and as the motors comprise considerable weight and cause environmental impacts on disposal. Furthermore, motors normally require electronic control systems which increase the cost, complexity, regulatory challenge.

The described display assembly can be used in any device which would benefit from displaying the relative position of components, especially if those components rotate relative to one another. The most relevant applications are in dispensing mechanisms, such as drug delivery devices like pen-type devices or injection-type devices, medical devices such as dispensers of antiseptic creams, analgesic creams, detergents and so on. Furthermore, this holds for applications in devices for dispensing adhesives, lubricants, paints, detergents and such like. Another example may relate to food dispensers for non-rigid foods such as e.g. tomato sauce, crushed garlic, cheese, butter, juice, smoothies, soup, coffee, tea, jam, peanut butter.

The described leadscrew may relate to any application which currently uses a plunger rod.

The term "drug", "substance" and/or "liquid medicament", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropin (Follitropin, Lutropin, Choriongonadotropin, Menotropin), Somatropin (Somatropin), Desmopressin, Terlipressin, Gonadorelin, Triptorelin, Leuprorelin, Buserelin, Nafarelin, Goserelin.

A polysaccharide is for example a glucosaminoglycan, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The scope of protection of the invention is not limited to the examples given hereinabove. The invention is embodied in each novel characteristic and each combination of characteristics, which particularly includes every combination of any features which are stated in the claims, even if this feature or this combination of features is not explicitly stated in the claims or in the examples.

REFERENCE NUMERALS

1 Cartridge
2 Indication member
3 Selection member
4 Housing
5 Drive member
7 Piston rod
8 Ratchet member
9 Dose member
10 Clutch element
11 Dose setting member
12 Actuation member
13 Resilient member
14 Clutch spring
15 Nut member
16 Plunger
17 Window
18 Proximal end
19 Distal end
20 Actuation feature
21 Ratchet feature
22 Teeth
23 Setting stop
24 Dispensing stop
25 Last dose feature
26 Auxiliary drive member
27 Ratchet spline
28 Indicium
29 Coupling member
30 Inner thread (housing)
31 Outer thread (ratchet member)
32 Actuation member spline
33 Dose member spline
34 Drive member support
35 Drug
36 Thread (piston rod)
38 Axial rib
39 Second direction
43 Piston rod feature
45 Masking section
46 Non-masking section
47 Coupling member window
48 Indication member thread
49 Actuation pin
50 Distal termination
51 Proximal teeth
52 Displayed section
53 Distal teeth
100 Drug delivery device
x Longitudinal axis

The invention claimed is:
1. A display assembly, comprising:
a body defining a window having an axial extension;
an indication member for providing information to be displayed in the window, wherein the indication member is movable relative to the body for changing the information displayed in the window; and
a selection member, wherein
the selection member defines a masking section and a non-masking section, the selection member is rotatable around a rotation axis with respect to the body and with respect to the indication member, the non-masking section and the masking section partially overlap with the window to define a displayed section of the indication member, and wherein the selection member and the indication member are coupled such that:

movement of the indication member with respect to the body is converted into rotational movement of the selection member with respect to the indication member and, wherein the displayed section of the indication member is axially displaced within the window.

2. The display assembly of claim 1, wherein the indication member is axially constrained but rotatable relative to the body.

3. The display assembly of claim 1, wherein the selection member is axially constrained relative to the body.

4. The display assembly of claim 1, wherein the indication member and the selection member are both rotatable around the rotation axis.

5. The display assembly of claim 1, wherein the non-masking section extends in the axial direction and in the angular direction.

6. The display assembly of claim 1, wherein the rotation axis and an axial extension direction of the window are aligned.

7. The display assembly of claim 1, wherein the indication member depicts a plurality of pieces of information, said plurality of pieces of information have a maximum axial extension along the indication member, the axial extension of the window and/or the non-masking section being greater than or equal to the maximum axial extension.

8. The display assembly of claim 1, wherein the indication member is an indication sleeve and the selection member is a selection sleeve, wherein the indication sleeve is retained in the selection sleeve.

9. The display assembly of claim 1, wherein the indication member and the selection member are coupled such that they rotate in a same direction or an opposite direction.

10. The display assembly of claim 1, wherein the selection member and the indication member are coupled by a coupling member.

11. The display assembly of claim 10, wherein the coupling member defines a coupling member window, the displayed section of the indication member being displayed through the coupling member window and the window.

12. The display assembly of claim 10, wherein the coupling member is threadedly coupled to the indication member, axially guided with respect to the body and guided along the non-masking section of the selection member.

13. The display assembly of claim 1, comprising a display driver which is coupled to the indication member or the selection member to drive movement of the respective member with respect to the body.

14. The display assembly of claim 1, wherein the window is formed by an opening in the body and the opening is covered either by a window insert connected to the body or by a label.

15. The display assembly of claim 1, wherein the selection member and the indication member are coupled such that:

rotational movement of the selection member with respect to the body is converted into movement of the indication member with respect to the selection member.

16. A drug delivery device comprising
a body defining a window having an axial extension; and
a display assembly comprising an indication member for providing information to be displayed in the window, wherein the indication member is movable relative to the body for changing the information displayed in the window; and
a selection member, wherein
the selection member defines a masking section and a non-masking section,
the selection member is rotatable around a rotation axis with respect to the body and with respect to the indication member,
the non-masking section and the masking section partially overlap with the window to define a displayed section of the indication member, and
the selection member and the indication member are coupled such that rotational movement of the selection member with respect to the body is converted into movement of the indication member with respect to the selection member,
wherein the displayed section of the indication member is axially displaced within the window, and wherein the display assembly provides a dose display mechanism to display a size of the dose which is set to be dispensed by the drug delivery device to a user through the window.

17. A display assembly, comprising:
a body defining a window having an axial extension;
an indication member for providing information to be displayed in the window, wherein the indication member is movable relative to the body for changing the information displayed in the window; and
a selection member, wherein
the selection member defines a masking section and a non-masking section,
the selection member is rotatable around a rotation axis with respect to the body and with respect to the indication member,
the non-masking section and the masking section partially overlap with the window to define a displayed section of the indication member, and
the selection member and the indication member are coupled such that rotational movement of the selection member with respect to the body is converted into movement of the indication member with respect to the selection member,
wherein the displayed section of the indication member is axially displaced within the window.

18. A method of setting a dose of a drug delivery device, the method comprising:
rotating a dose setting member to set a dose, the dose setting member:
(a) rotating an indication member having a plurality of dose indication markings and
(b) axially moving a coupling member having a window, the window framing one of the plurality dose indication markings corresponding to the set dose, the coupling member rotating a selection member with respect to the indication member.

* * * * *